(12) United States Patent
Boxen

(10) Patent No.: US 6,271,510 B1
(45) Date of Patent: Aug. 7, 2001

(54) FIBER OPTIC GAMMA CAMERA HAVING SCINTILLATING FIBERS

(76) Inventor: Izzie Boxen, 117 Old Surrey Lane, Richmond Hill, Ontario (CA), L4C 6R8

( * ) Notice: Subject to any disclaimer, the term of this patent is extended or adjusted under 35 U.S.C. 154(b) by 0 days.

(21) Appl. No.: 09/372,128

(22) Filed: Aug. 11, 1999

Related U.S. Application Data

(60) Provisional application No. 60/112,776, filed on Dec. 18, 1998.

(51) Int. Cl.[7] .................................................. H01L 27/00
(52) U.S. Cl. ..................................... 250/208.1; 250/227.2
(58) Field of Search ........................... 250/208.1, 207, 250/214 R, 227.2, 363.06, 363.1, 363.01–363.05, 214 VT, 216; 313/532, 534, 103 R, 103 CM; 378/21

(56) References Cited

U.S. PATENT DOCUMENTS

| | | | |
|---|---|---|---|
| 3,668,396 | * 6/1972 | Asars et al. | 250/214 VT |
| 4,415,810 | 11/1983 | Brown, Sr. | 250/484.1 |
| 4,933,961 | 6/1990 | Rushbrooke et al. | 378/57 |
| 5,308,986 | 5/1994 | Walker | 250/370.11 |
| 5,325,855 | 7/1994 | Daghighian et al. | 128/653.1 |
| 5,636,299 | 6/1997 | Bueno et al. | 385/15 |
| 5,682,411 | 10/1997 | Rushbrooke et al. | 378/98.3 |
| 5,719,401 | 2/1998 | Chaney et al. | 250/370.1 |
| 5,729,640 | 3/1998 | Castonguay | 382/321 |
| 5,793,046 | 8/1998 | Jeffers et al. | 250/364 |
| 5,802,236 | 9/1998 | DiGiovanni et al. | 385/127 |

FOREIGN PATENT DOCUMENTS

| | | |
|---|---|---|
| 0323324 | 5/1989 | (EP) . |
| WO 94/23458 | 10/1994 | (WO) . |

OTHER PUBLICATIONS

Lee, Lap Yen et al. "Multi–strip Scintillation Counters (MSSC)", Nuclear Instruments and Methods, vol. 119, No. 1, 1974, pp. 29–33, XP002135485 amserdam, nl, Feb. 1974.

* cited by examiner

Primary Examiner—Que T. Le
(74) Attorney, Agent, or Firm—Bereskin & Parr

(57) ABSTRACT

Apparatus for capturing two-dimensional images created by radioactive emanations, such as gamma rays, from a radioactive source, comprises a collimator, a two-dimensional array of scintillating fibers, and position encoding apparatus. The scintillating fibers are located at preselected x and y positions in an x-y plane. The position encoding apparatus comprises banks of photon detectors and a network of optical fibers which are connected to the photon detectors in a manner which encodes the x-y coordinates of the scintillating fibers, and a signal processor for generating position signals indicative of the encoded position of an active scintillating fiber.

24 Claims, 5 Drawing Sheets ical imaging systems, and
FIBER OPTIC GAMMA CAMERA HAVING SCINTILLATING FIBERS This application claims benefit of Provisional Application 60/112,776 filed Dec. 18, 1998.

FIELD OF THE INVENTION

This invention relates to radiation imaging systems, and in particular, to gamma ray cameras for use in the field of nuclear medicine.

BACKGROUND OF THE INVENTION

There are a number of different types of radiation imaging systems currently in use in the field of nuclear medicine. The most common type of systems, known as Anger gamma ray cameras, comprise a collimator, a scintillation crystal which emits photons when struck by gamma rays, and an array of photomultipliers tubes and associated electronics which detect the photons. Anger cameras have been used for many years for various applications including the imaging of gamma rays emitted by a radionuclide put into a patient. The sensitivity and resolution of Anger gamma cameras are determined by a number of factors, such as radionuclide used, patient geometric factors (distance, attenuation, scatter, distribution), camera collimator, detecting scintillation crystal, electronics/circuitry and computer/display. Most gamma cameras are designed to give the best combination of sensitivity and resolution at about 140 keV, the energy of the major gamma ray photon coming from technetium-99m (99mTc, $^{99m}$Tc, Tc-99m), the commonest radionuclide presently used in nuclear medicine.

Various efforts have been made to improve the sensitivity and resolution of Anger gamma cameras. Camera sensitivity can be improved by the use of thicker detection crystals, scintillation crystal materials with greater stopping power, and more sensitive collimators and photomultiplier tubes (PMTs). However, the use of thicker crystals and high sensitivity collimators results in loss of resolution. Conversely, improved resolution of the system in prior art Anger designs results in loss of sensitivity. Efforts at improved resolution are usually geared towards using a thinner crystal, higher resolution collimator (with smaller holes packed closer together) or electronics/computer "acceptance" of summation energy detected (usually called the "Z" peak) within a narrower acceptance range (in an attempt to reduce acceptance of scattered photons). However, the sensitivity and resolution of Anger cameras remain poor, especially for higher energy gamma rays. The present best intrinsic resolution of Anger gamma cameras for 99m-Tc is about 3 mm.

Other types of radiation imaging cameras, such as positron emission tomography (PET) cameras, are designed for a specific use and cannot be used for planar imaging or imagining other radionuclides. PET cameras use fixed-ring, thick bismuth germinate crystals, and are very expensive. Recent "hybrid" gamma cameras use thick crystals, very heavy (and expensive) collimators and coincidence circuitry to image positron emitters, but the sensitivity of such cameras is at best 10% that of a dedicated PET system and the resolution at least twice as bad.

There is a lower and upper limit to how much radioactive material can be given to a patient (injected, inhaled, eaten, etc.) in order to see, by gamma camera, how it is handled by the body. The lower limit is determined by the sensitivity of the gamma camera and by the amount of interfering background radiation, and must be great enough to yield acceptable diagnostic imaging or information. The maximal amount is determined, for one, by radiation safety, which specifies that only the minimal amount be used that gives acceptable diagnostic imaging or information.

However, there are other reasons for limiting the maximum amount of radioactive material given to patients. While the gamma camera system (crystal, electronic circuitry and computer) is busy "registering" an event (scintillation in the crystal, signifying interaction with a gamma ray), it is incapable (absolutely or relatively) of responding to another event. This "dead time" for most gamma cameras is of the order of or greater than a micro-second. For higher amounts of radioactivity the proportion of dead time to mean time between events rises in a non-linear fashion. Many electronic systems are also "saturable", i.e. beyond a certain event rate they simple do not respond at all. Any attempt at quantitating amounts of radioactivity present in certain areas in relation to others gives rise to dead time errors which are very large for higher amounts of radioactivity. Also, events (gamma ray interactions producing crystal scintillations) that occur very close in time give rise to a summation scintillation whose total energy (Z-pulse) is well outside the acceptance window and is rejected by the computer as not coming from the gamma ray of interest. This coincidence pile-up, like dead time, also effectively reduces detected count rate in comparison with flux.

Limiting radioactivity to avoid coincidence and dead time errors gives rise to increased statistical errors since radioactivity obeys Poisson statistics. The standard deviation in counts for Poisson statistics is the square root of the counts observed (in any region or time interval). Minimizing quantitation errors therefore requires balancing the effects of too low a count rate against those of too high a count rate. Prior art Anger gamma camera imaging in patients introduces quantitation errors of at least 5%, under the best circumstances. Much higher count rate capabilities would be helpful, since, with many radionuclides, the radiation safety limits are far from being reached.

The collimator is often a major factor affecting resolution in prior art Anger gamma camera imaging, while the crystal is often the major factor reducing sensitivity, although both collimator and crystal influence sensitivity and resolution greatly. Dead time and coincidence losses are mostly due to the large crystals used in Anger gamma cameras (up to about 500 mm) and the fact that each PMT receives scintillation light from the entire crystal.

There is accordingly a need for an improved gamma camera having better resolution, sensitivity, and linearity of response.

SUMMARY OF THE INVENTION

The present invention is directed towards apparatus for capturing a two dimensional image created by particle emanations, such as gamma rays, emitted from a radioactive source. The camera apparatus comprises collimator means for collimating the particle emanations and producing collimated emanations, scintillating means aligned behind the collimator means for capturing the collimated emanations and generating scintillation photons corresponding thereto, comprising a two-dimensional array of scintillating fiber optics (SFO), and position encoding means for encoding the position of a scintillating fiber receiving an emanation within a pre-selected time interval. The collimator means comprises a collimator plate having a series of collimator apertures separated by septa made of a material capable of absorbing the emanations. Each scintillating fiber is located at a pre-selected x-position and y-position having x-y coordinates in an x-y plane. The position encoding means comprises photon detecting means for detecting the emitted scintillation photons and generating output signals correlatable therewith, optical coupling means for optically coupling each scintillating fiber to the photon detecting means in a manner which encodes the x-y coordinates of the scintillating fibers, and processing means for processing the output signals and generating position signals indicative of the encoded position of the active scintillating fiber.

The optical coupling means preferably comprises a network of optical fibers comprising a set of position fibers coupled to each individual scintillating fiber representing the x and y coordinates of the position thereof. The photon detecting means preferably comprises banks of photon detectors wherein each bank of photon detectors comprises a plurality of individual photon detectors, preferably photomultiplier tubes. The sets of position fibers preferably comprise individual position fibers having input ends coupled to the scintillating fiber and output ends coupled to a pre-selected combination of individual photon detectors representing the coordinates of the position of the scintillating fiber.

BRIEF DESCRIPTION OF THE DRAWINGS

The invention will now be described by way of example only, by reference to the following drawings, in which.

DETAILED DESCRIPTION OF PREFERRED EMBODIMENTS

Figure 1:
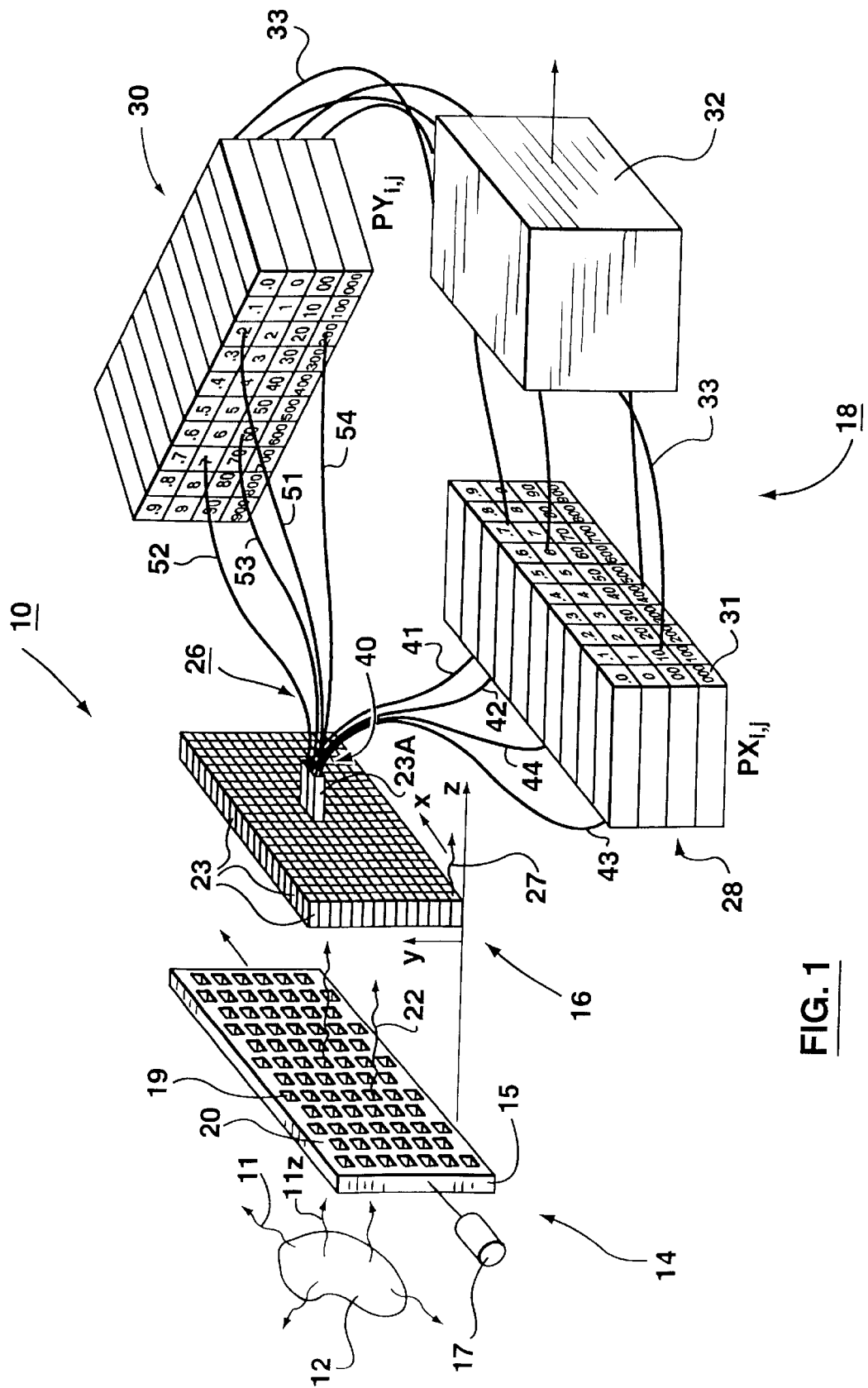
FIG. 1 is a diagrammatic view of a fiber optic gamma camera, made in accordance with a preferred embodiment of the subject invention.

Referring to FIG. 1, illustrated therein is a fiber optic camera apparatus 10 made in accordance with a preferred embodiment of the subject invention. Camera apparatus 10 captures the images created by particle emanations such as gamma rays 11 emitted from a radiation source 12, typically a radionuclide put into a patient. As used herein, the term "particle emanations" includes gamma rays and other photons, and material particles such as electrons, protons and neutrons, and the term "gamma ray" includes various radioactive emanations such as x-rays and other ionizing radiation. Gamma camera apparatus 10 comprises a collimator 14, a scintillation plate 16, and scintillating fiber position encoding means shown generally as 18.

Collimator 14 comprises a collimator plate 15 extending in an x-y collimator plane, made of lead or other gamma ray absorbing material. Collimator plate 15 comprises an array of collimator apertures 19 arranged in collimator rows and columns. Adjacent apertures 19 are separated by septa 20 of sufficient width and thickness to absorb incident off-axis gamma rays 11. Axial gamma rays 11z travelling in the z-direction pass through apertures 19, thereby creating collimated gamma rays 22. Collimator 14 is preferably a dynamic collimator such as that disclosed in the applicant's co-pending application entitled "Dynamic Collimators", filed on Aug. 11, 1999 under Ser. No. 09/372,071 comprising drive motor 17 which moves collimator plate 15 in the x-direction.

Scintillation plate 16 is aligned behind collimator 14, and extends in an x-y scintillation plane parallel to the collimator plane. Scintillation plate 16 comprises an array of scintillating fibers 23, which capture collimated gamma rays 22 and emit scintillation photons corresponding thereto. Each scintillating fiber 23 is located in a known x-y position in the scintillation plane. The rows of scintillating fibers 23 of scintillation plate 16 are aligned with the rows of collimator apertures 19 of collimator plate 15 such that an aperture 19 sequentially registers with a number of scintillating fibers 23 in a given row, as collimator plate 15 is moved in the x-direction by drive motor 17.

Scintillating fiber position encoding means 18 encodes the x-y position of each scintillating fiber 23 receiving a gamma ray 22 within a pre-selected time interval. Encoding means 18 comprises fiber optic coupling means 26, x-bank of photon detectors 28, y-bank of photon detectors 30, and signal processor 32. Fiber optic coupling means 26 comprises a network of individual regular optical fibers 39 which optically couple scintillating fibers 23 to banks of photon detectors 28, 30, in a manner which encodes the positions of scintillating fibers 23 in the x-y coordinates.

Banks of photon detectors 28, 30 detect scintillation photons 27 generated by scintillating fibers 23 and generate detector signals correlatable therewith. Banks of photon detectors 28, 30 are preferably arrays of photomultiplier tubes (PMTs) 31, although they could comprise other photon detection devices, such as a large array avalanche photodiode (LAAPD). The output terminals of PMTs 31 are electrically coupled to signal processor 32 by output signal cables 33.

Signal processor 32 comprises input means for receiving the output signals from PMTs 31, and electronic circuitry or computer which processes the output signals from PMTs 31, and generates position signals indicative of the encoded position of the active scintillating fiber. Signal processor 32 also comprises coincidence circuitry to determine whether exactly one PMT from each row in banks 28 and 30 generates a signal during a given time period.

Figure 2:
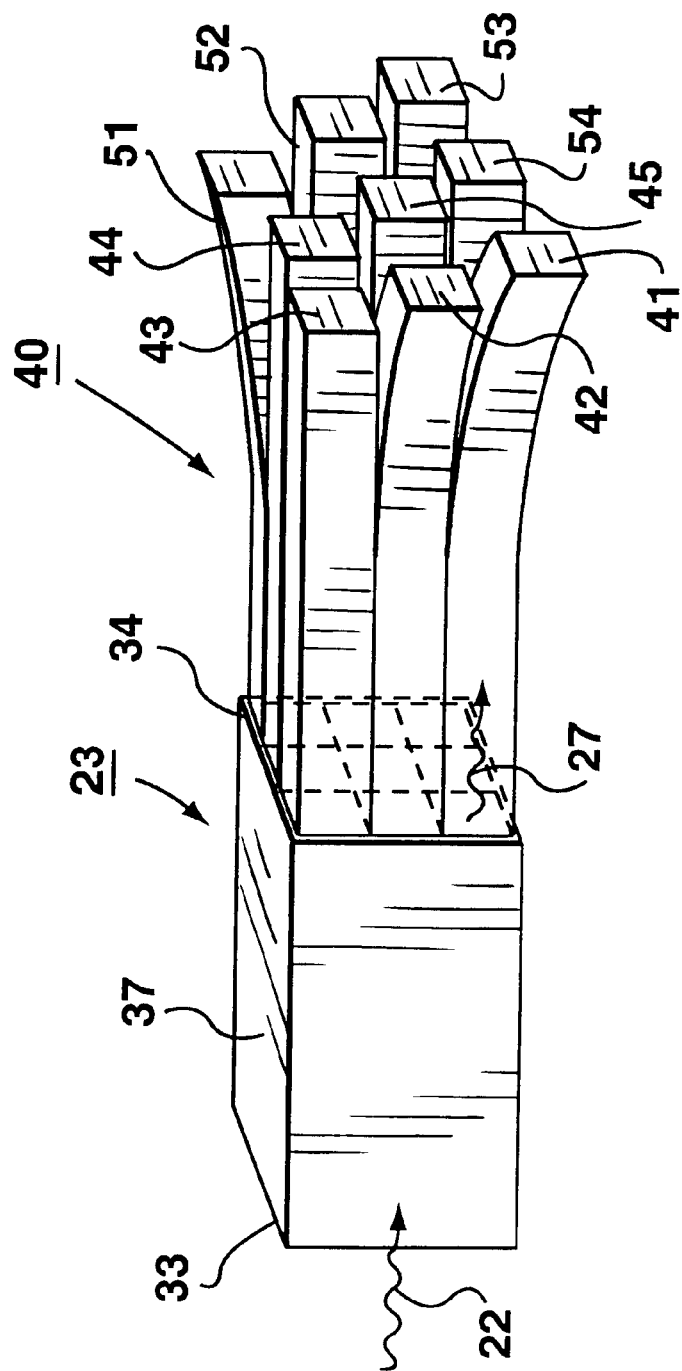
FIG. 2 is a perspective view of a typical scintillating fiber and associated fiber optic bundle of the preferred embodiment.

Referring now to FIG. 2, each scintillating fiber 23 is preferably of square cross-section, having an imaging face 33 for receiving gamma rays 22 and a photon emitting face 34 for emitting scintillation photons 27. Scintillating fiber 23 is preferably a glass scintillator which incorporates scintillating chemicals that will react predominantly by the photoelectric effect, which, for large enough diameter of SFO, results in all of the energy of the gamma ray 22 being transformed into scintillation photons 27. The use of such scintillating fibers 23 allows for the imaging of radiation sources 12 with an intrinsic resolution the width of these fibers and also allows measurement of the energy of collimated gamma rays 22. The importance of measuring this energy lies in the necessary ability to discriminate gamma rays 22 from extraneous photons, predominantly scattered photons. These extraneous photons can come from far away from the radionuclides in source 12 and from any direction. Failure to eliminate scattered and other unwanted photons from photon detectors 28, 30 results in a blurred image.

Scintillating fibers 23 preferably have high stopping power for the photons being imaged and are long enough to give close to 100% interaction efficiency for the highest energy gamma rays of interest. The diameter of the scintillating fibers 23 is determined by the resolution desired. For a resolution of 1 mm the diameter would be 1 mm.

Scintillating fiber 23 preferably includes an outer coating 37, made of a gamma-reflective material such as magnesium oxide or titanium oxide (which scatters light in all directions) to increase the number of photons arriving at PMTs 31. Reflective coating 37 obviates the need for extra mural absorption fibers and improves intrinsic resolution to the diameter of a single scintillating fiber. Imaging face 33 usually has a metal or metal alloy coating to reflect photons back towards the other end, also to increase the number of detected photons.

The optical fibers are grouped into sets of optical fibers associated with each scintillating fiber 23. Optical fiber set 40 comprises nine regular optical fibers of square cross-section, having input ends coupled to the emitting end 34 of scintillating fiber 23. As shown, regular optical fibers 41–44 are used to encode the x-position of scintillating fiber 23, and regular optical fibers 51–54 are used to encode the y-position of scintillating fiber 23. Central optical fiber 45 is optional, and may be used to record the energy of gamma ray 22. A square cross-section allows for efficient collection of scintillation photons 27 and accurate measurement of gamma ray energy. The cross-section of emitting end 34 of scintillating fiber 23 should match the cross-section of fiber optic set 40, to maximize transfer of scintillation photons 23 to fiber optic set 40.

Figure 3:
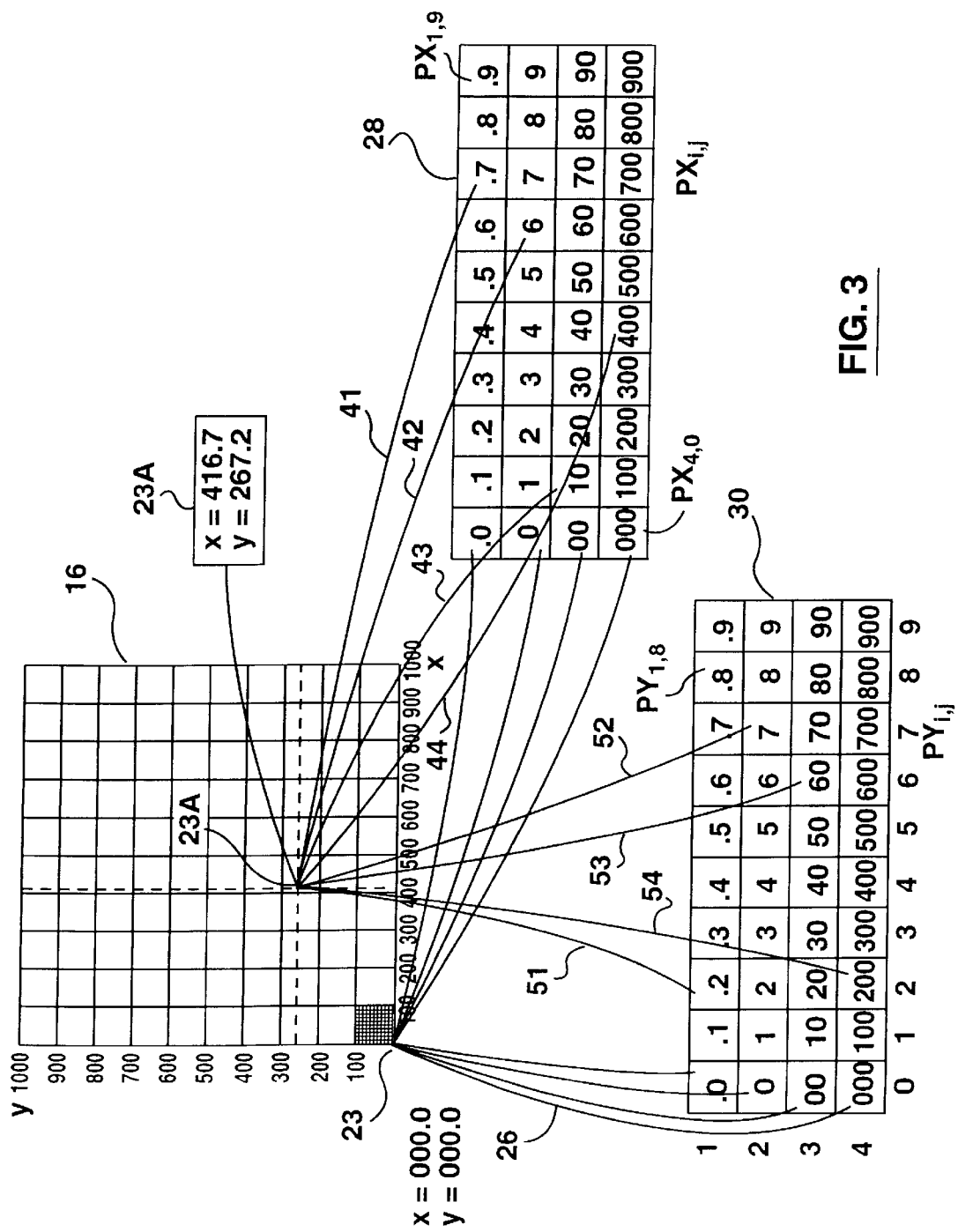
FIG. 3 is a diagram illustrating the matching scheme used by the position encoding means of the preferred embodiment.

Referring to FIG. 3, illustrated therein is a base 10 version of position encoding means 18, having a 1000 mm by 1000 mm field of view with 0.1 mm resolution. To achieve this resolution, the diameter of each scintillating fiber 23 must be 0.1 mm. X-bank of photon detectors 28 comprises 40 PMTs $PX_{i,j}$, and y-bank of photon detectors 30 comprises 40 PMTs $PY_{i,j}$, for a total of 80 PMTs. Each fiber optic set 40 comprises a 3×3 array of fiber optics attached to the emitting end 34 of scintillating fiber 23.

Each bank of PMTs $PX_{i,j}$ and $PY_{i,j}$ is structured such that each row i of PMTs represents a particular decimal place of the x or y position coordinates, and the individual PMT j in a given row represent the value of that decimal place. Thus PMT $PX_{1,0}$ is the PMT in the first row, zeroth column of x-bank of photon detectors 28, and represents the 0.0 mm value for the first decimal place of the x-position coordinate, PMT $PX_{1,1}$ represents the 0.1 mm value of the first decimal place, PMT $PX_{1,2}$ represents the 0.2 mm value, and so on, with $PX_{1,9}$ representing the 0.9 mm value of the first decimal place of the x-position coordinates. Similarly, PMTs $PX_{2,0}$ through $PX_{2,9}$ are the PMTs in the second row of x-bank 28, which represent the 0 mm, 1 mm, 2 mm, . . . , 9 mm values of the second decimal place for the x-position coordinates. PMTs $PX_{3,0}$ through $PX_{3,9}$ represent the 00 mm, 10 mm, 20 mm, . . . , 90 mm values for the third decimal place of the x-position coordinates, and PMTs $PX_{4,0}$ through $PX_{4,9}$ represent the 000 mm, 100 mm, 200 mm, . . . , 900 mm values for the fourth decimal place of x-position coordinates, for a total of 40 PMTs for x-position coordinates. Likewise, PMTs $PY_{1,0}$ through $PY_{1,9}$ represent the 0.0 mm through 0.9 mm values for the y-position coordinates, PMTs $PY_{2,0}$ through $PY_{2,9}$ represent the 0 mm through 9 mm values for the y-position coordinates, PMTs $PY_{3,0}$ through $PY_{3,9}$ represent the 00 mm through 90 mm values for the y-position coordinates, and PMTs $PY_{4,0}$ through $PY_{4,9}$ represent the 000 mm through 900 mm values for the y-position coordinates.

The output ends 55 of position fibers 41–44 and 51–55 for each scintillating fiber 23 are optically coupled to a combination of individual PMTs which represent the coordinates of the x-position and y-position for each such scintillating fiber 23. In the example shown in FIG. 1, scintillating fiber 23A is located at an x-position having the x-coordinate 416.7 and at a y-position having the y-coordinate 267.2. Therefore, x-position fiber 41 is coupled to $PX_{1,7}$ having the value 0.7, x-position fiber 42 is coupled to $PX_{2,6}$, having the value 6, x-position fiber 43 is coupled to $PX_{3,1}$ having the value 10, and x-position fiber 44 is coupled to $PX_{4,4}$ having the value 400. Likewise, y-position fibers 51–54 are coupled to $PY_{1,2}$, $PY_{2,7}$, $PY_{3,6}$ and $PY_{4,2}$, respectively.

The output ends of the sets of position fibers associated with the other scintillating fibers are likewise connected to the combination of individual PMTs which corresponds to their respective position coordinates. Thus each PMT will have connected to it a bundle of position fibers. The bundles of output ends of the position fibers are tapered, to enable them to be optically coupled to a single PMT.

Signal processor 32 uses the signals from the PMT banks to determine the x and y positions and also sums the voltage output (Z-pulse) within fixed time intervals to determine the gamma ray energy. The signal processor 32 may include coincidence circuitry to accept or reject signals. Only if exactly one PMT from each row of the x-bank 28 and y-bank 30 sends a signal within a time interval, and only if the gamma ray energy is within specified values, are these X, Y and Z pulses passed onto a memory buffer in a computer for further computer processing. Alternatively, the signals can be passed indiscriminately to the memory buffer along with time pulse signals for analysis and processing by the computer later. This technique is less demanding of the signal processor 32. Present coincidence circuitry can process signals within time intervals as little as $10^{-9}$ sec.

As noted above, only a maximum of 8 of the 9 fibers in the set are needed for the above position encoding. The central (9th) fiber is the one best suited for omission, because of symmetry of accessibility of the others and because of symmetry in probability of distribution of photons in the scintillating fiber.

Alternatively, if 1 mm resolution is desired for a 1000 mm by 1000 mm field of view, 1 mm scintillating fibers can be used with a total of 60 PMTs. Slight variations can be made for rectangular fields of view. For example, a 100 mm (x-direction, say) by 1000 mm (y-direction, say) field of view with 0.1 mm resolution could be obtained by using 30 PMTs for the x-positions and 40 PMTs for the y-positions, based on the above position-encoding method. Such a set-up could be used as a scanning imager to reduce size and cost, but would only be practical if scanning times were acceptable.

Figure 4:
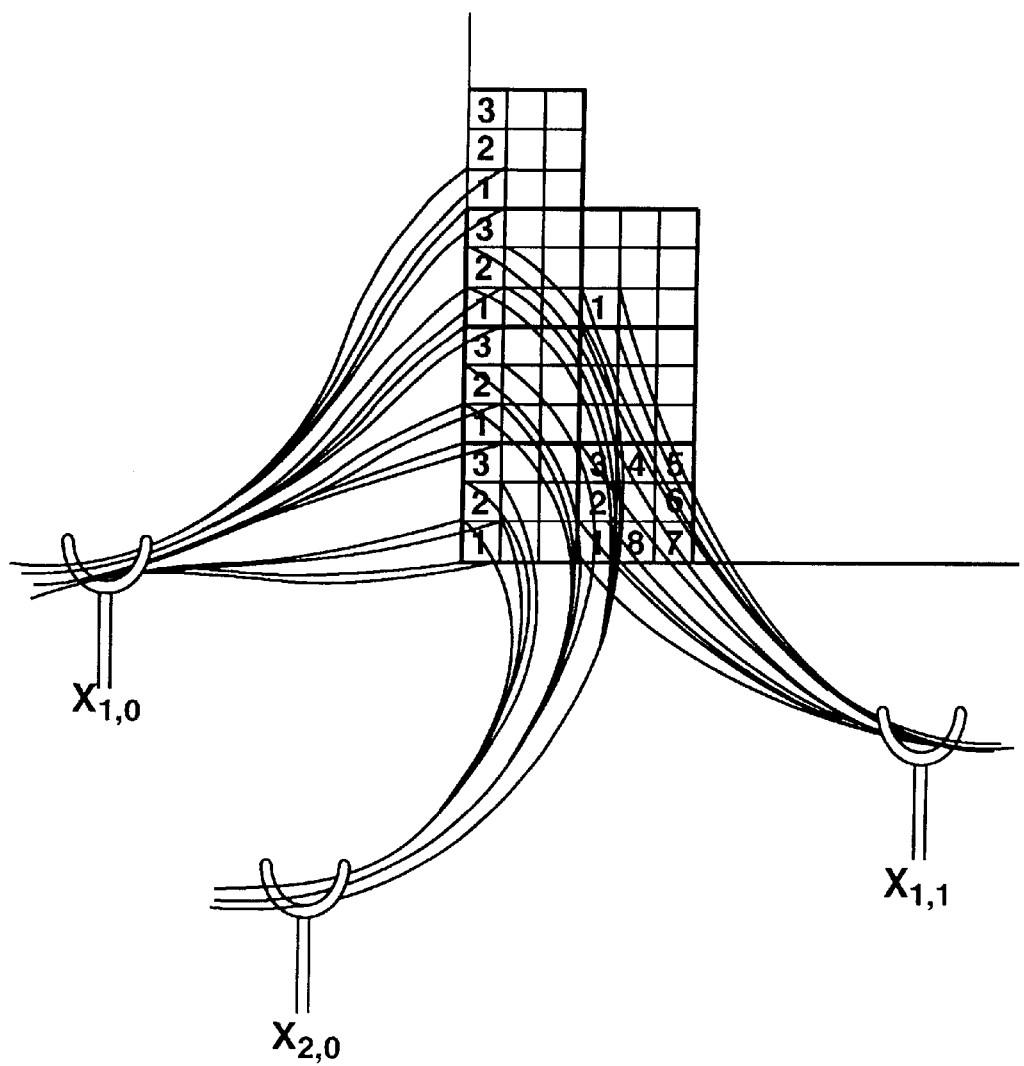
FIG. 4 is a diagram illustrating the method for connecting the optical fiber bundles to the scintillating fibers and photon detectors of the preferred embodiment.

Referring now to FIG. 4, one possible base-10 connection process for a 3×3 array of position fibers, sufficient for a 10,000 by 10,000 scintillating fiber optic plate, is outlined below (same general method could be used for 2×2 or other size position fiber sets and other bases). In this case, there are 4 rows of 10 PMTs each for the x-positions and the same for the y-positions. For each PMT there is a cradle to hold the bundle of fibers until they are ready for (any further processing before) attachment. The cradles (possibly moveable) are held in such an array and far enough apart that physical interference of the fibers is kept to a manageable amount. Any pre-tapering of the fibers would assist in this. The final positions of the PMTs are also such as to keep this interference manageable and to allow access to each PMT and its attached fiber optic bundle separately.

Robotics connect with optical glue, a single plastic optical fiber to the same position, say 1 as shown, on emitting end of each of the 10,000 scintillating fibers in the first column of scintillating plate 16, called, say, $x_0$ (nomenclature to designate x-position), and group the other ends of these optical fibers together into a loose bundle in a cradle, called $X_{1,0}$, which will in due course be optically coupled to PMT $PX_{1,0}$.

This is repeated for positions 2, 3 and 4 to give bundles in cradles labelled $X_{2,0}$, $X_{3,0}$ and $X_{4,0}$, respectively. This nomenclature so far designates the zero x-position PMT in each of the 4 rows. The nomenclature for additional cradles will be $X_{i,j}$, where i=1, 2, 3, 4 is the PMT row and j=0, 1, . . . , 9 designates the PMT in that row.

For columns $x_1, \ldots, x_9$ fibers from all the 1-positions are added to the respective cradles $X_{1,1}$, $X_{1,3}$, $X_{1,4}$, $X_{1,5}$, $X_{1,6}$, $X_{1,7}$, $X_{1,8}$, $X_{1,9}$. Fibers from all the 2-positions for columns $x_0, \ldots, x_9$ are added to cradles $X_{2,0}, \ldots, X_{2,9}$, respectively, fibers from all the 3-positions are added to cradles $X_{3,0}, \ldots, X_{3,9}$, and fibers from all the 4-positions are added to cradles $X_{4,0}, \ldots, X_{4,9}$.

For column $x_{10}$, the 1-position fibers are added to cradle $X_{1,0}$, the 2-position fibers are added to cradle $X_{2,1}$, the 3-position fibers are added to cradle $X_{3,0}$, and the 4-position fibers are added to cradle $X_{4,0}$.

In general, for $m = j_1 \times 10^0 + j_2 \times 10^1 + j_3 \times 10^2 + j_4 \times 10^3$, $m = j_4 j_3 j_2 j_1$, the standard decimal notation. For column m, fibers from the 1-positions are added to cradle $X_{1,j1}$, fibers from the 2-positions are added to cradle $X_{2,j2}$, fibers from the 3-positions are added to cradle $X_{3,j3}$, and fibers from the 4-positions are added to cradle $X_{4,j4}$.

Once all of the fibers are added to their respective cradles $X_{i,j}$, all of the fibers of each cradle $X_{i,j}$ are optically coupled to their respective PMT $PX_{i,j}$.

The same process is used to create the 40 y-position encoding bundles, using positions 5–8. For practical purposes of minimizing physical interference, all the x and y position fibers in a given row (or column) are connected to that row (or column) before doing so for the next row (or column).

The exact number of rows and columns does not affect the above general process. In general, for P the base (the number of PMTs in each row) and f the number of x position-encoding fibers (and also of y positions), the maximum number of x positions (and of y positions) encoded would appear to be $P^{f}-1$, but the x=0 (and y=0) position accounts for the extra 1, so that all $P^f$ xpositions (and also y positions) are actually encoded. The above nomenclature could have been changed to account for this, but the simplified symmetry of the nomenclature used would have been lost, making following of the above more difficult.

For a larger number of scintillating fibers in the scintillating plate, tapering may be necessary to fit the position-encoding optical fibers to the PMTs.

Since this type of encoding and hook-up, if done by hand, would be fairly labor-intensive and prone to physical damage to the fibers, robotics is preferred. Use of optical gel to removably fix a position bundle to a PMT would facilitate removal of the PMT and replacement for repairs. Hopefully, the fibers themselves would never be damaged, since replacement in the field for such a set-up would be very labor intensive. A less labor-intensive technique would be to make identical small sections of scintillation-regular optical fiber combination by machine/computer/robotics, say 10 mm by 10 mm square, and then to put them together by hand. This would necessitate a mechanical means of holding these together firmly (e.g. an indentation on two opposite sides to allow positioning along a rigid bar). The optical fiber bundle in a small section would have to be fairly pliable and long enough to allow cutting to length and polishing later. This would also facilitate replacement of damaged fiber sections. The fiber bundles to each PMT would have to be cut a little longer than actually needed on initial manufacturing to allow for additional polishing in the field if replacement is needed for any portion. Using robotics to make the full imaging fiber face would be faster, cheaper and easier, but would not allow easy replacement of damaged fiber sections in the field.

Because of the statistical nature of imaging (or detecting) gamma rays (or any radiation particle), there is a lower limit on resolution, even in theory, determined by the flux of imaged gamma rays (or other radiation particles) in comparison with the flux of interfering background radiation. The practical considerations of radiation safety and time required for imaging will also limit the attainable resolution when imaging patients. Such practical limitations on resolution will be determined, for the most part, by empirical means. There is no point spending extra time and money using fiber diameters less than this limitation, if only diagnostic imaging is to be done with a camera. The design considerations discussed are made ignoring such patient constraints and assuming that the flux of imaged gamma rays is high enough to allow the discussed manipulations to be effective. Animal research work, in which radiation flux and imaging time constraints are much less stringent than in patient imaging, would be expected to benefit more.

Where body motion cannot be avoided, such as in the chest and upper abdomen (because of breathing), motion correction imaging algorithms will be more important than in the past.

Depending on the size and shape of field of view and the resolution desired, it might be more efficient to use the octal, hexadecimal or other bases for PMT position encoding. For example, consider a (small) field of view imaged by a 256 by 256 scintillating fiber plate. Position encoding in the x-direction as above in base 10 would need 10 PMTs each for the units ($10^0$) and 10s ($10^1$) position banks and 2 for the 100s ($10^2$) position bank, for a total of 22. Similarly, for the y-direction a total of 22 PMTs would be needed, giving a total of 44 PMTs to encode the (x,y) positions. In base 2 the x-positions could be encoded by two PMTs each in the units ($2^0$), 2s ($2^1$), . . . , and 128s ($2^7$) position banks, for a total of 16 PMTs. Including the y-positions, a total of 32 PMTs would be needed, a savings of 12 PMTs over the base 10 hook-up. However, the position-encoding fiber optic bundle would have to be a 4×4 bundle, i.e. would have to have 8 fibers for x-positions and 8 for y-positions. Correspondingly fewer regular fiber hook-ups to position PMTs would be needed. Such a set-up with 1 mm resolution (and therefore scintillating fibers of 1 mm diameter) may be ideal for imaging thyroid, heart, head, other small localized areas of the body or for small animal studies.

Figure 5:
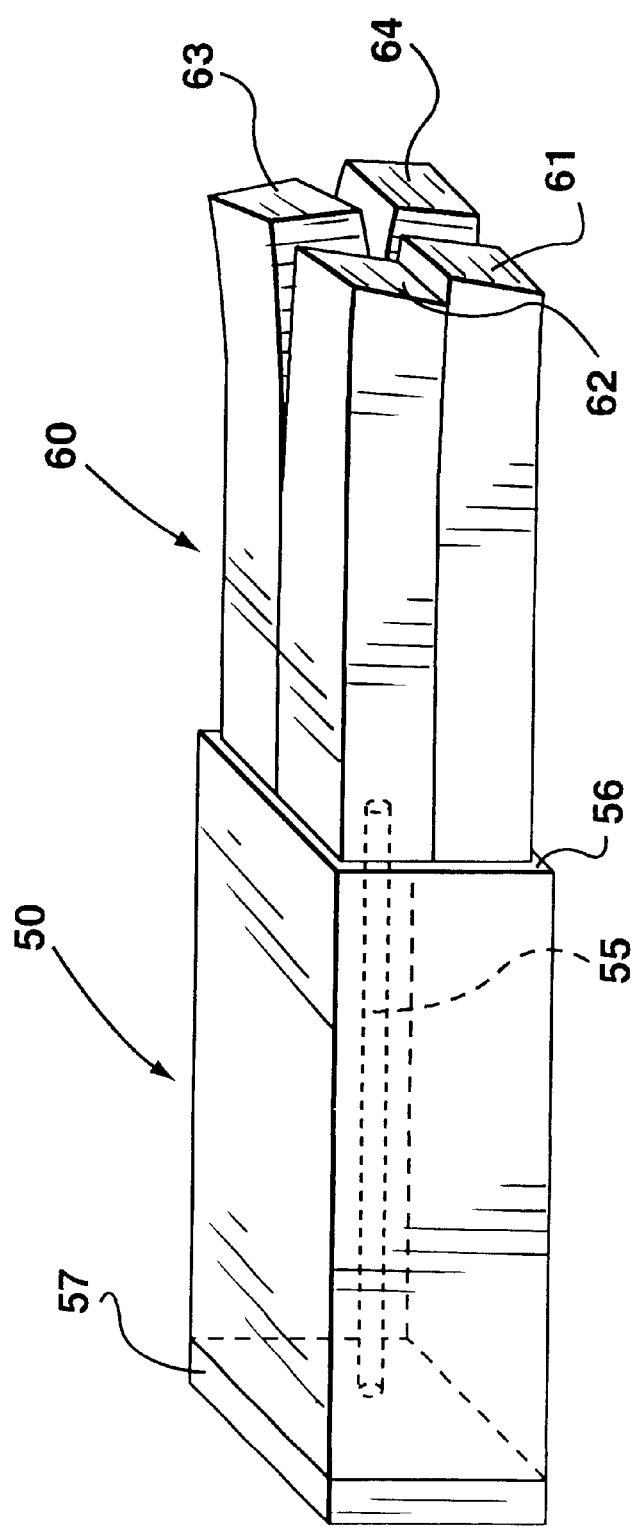
FIG. 5 is a perspective view of a scintillating fiber and fiber optic bundle of an alternative embodiment of the invention.

Referring now to FIG. 5, shown therein is an alternative embodiment of the subject invention, comprising a conductive scintillating fiber 50 coupled to a position encoding fiber optic bundle 60 comprising a 2×2 array of regular optical fibers 61–64.

Scintillating fiber 50 includes an outer layer of conducting material 52 and a thin conducting, transparent (to the scintillation photons) central electrode 55. Outer layer 56 is charged negatively, i.e. by applying a negative voltage thereto, and central electrode 55 is kept at zero potential. Central electrode 55 could be a conducting optical fiber, which could be brought out separately into a bundle and grounded, but it is easier to have the ends of all fibers 55 in contact with a grounded thin plate of same material at the front or back end of the scintillating fiber plate. Easier still, especially to avoid interference with position-encoding fibers attached to the back end of the scintillating fiber plate, is to have these central electrodes contact the metallic (used for reflection) front end coat 57 and keep this coat grounded. A short gap of non-conducting coating around the front ends of the scintillating fibers would be needed to prevent shorting. Alternatively, the outer conducting coat can be dispensed with and only the central conducting fibers used if kept at positive potential. This obviates the need for an insulating gap around the front end of each scintillating fiber. The greater the magnitude of this voltage, the closer to the fiber axis the ejected electrons would be kept and the smaller the scintillation sphere (actually now an ovoid). This would allow maintaining ability to measure gamma ray energy with scintillating fibers much narrower than 1 mm and so ability to reject scattered photons. Such an embodiment would only be needed if gamma ray energy calibration could not be done accurately enough without a more complete collection of scintillation photons.

An expected benefit is more complete and therefore more accurate gamma ray energy detection, reducing energy resolution to significantly better than the past art value of 15–20% for most Anger gamma cameras. Because of the light reflection and propagation characteristics, a square cross-sectional scintillating fiber optic shows uniform response for gamma rays interacting anywhere within its cross-section, whereas a round fiber does not. A square scintillation fiber is therefore the preferred one. The greatest benefit in energy resolution would be expected with higher energy photons, as occur with PET imaging. The outer conducting or non-conducting material can also act as a collimator, especially if the dynamic collimator confines the entering gamma rays to a narrow enough angle.

Alternatively, the central conducting electrode 55 could be a very fine metal fiber. If its diameter is less than ½ the wave length of the main scintillation photons, then no unwanted central absorption or scatter of these photons will occur. Such narrow metal fibers may be difficult to incorporate using present art. Whether metal or not, a central conducting fiber will absorb some of the electrons, necessitating an additional reason for energy-calibration of the instrument. From probabilistic considerations, the fraction of electrons absorbed in this way is expected to have a fixed mean and variance, both being dependent on the gamma-ray energy, material used for scintillating fibers, voltage applied and geometry. This may impede improvement in energy resolution. Experimentation will be needed to check on this and to see if this also puts a lower practical limit on fiber diameter and thereby image resolution. U.S. Pat. No. 5,793, 046 discloses a technique of coating an optical fiber with coloring matter dopants that give off visible range photons when excited by electrons. Such a technique could be used to convert and capture the energy of electrons emitted in a scintillating fiber that reach a wall, and so increase the total energy collected, improving energy resolution. This may obviate the need for a charged central core and would eliminate the loss of any electrons to such a core.

Using a 2×2 position-encoding fiber optic set may offer some advantages over other arrays. A 2×2 regular fiber optic set (square array of square fibers) attached to a square scintillating fiber optic (SFO) (of the same total cross-section) yields complete symmetry of scintillation photons entering the position-encoding fibers, within statistical fluctuation, and also allows more scintillation photons per position-encoding fiber than connections with a greater number of fibers in the bundle. The statistics and uniformity of PMT response are therefore improved. However, only 2 rows of PMTs in the x-position bank and 2 rows in the y-position bank can be encoded this way. If the SFO plate consists of N×N fibers and each bank row has P PMTs, then $P^2=N$. If SFOs are used in a 256 by 256 array, then each bank row would consist of $N^{1/2}=256^{1/2}=16$ (i.e. base 16 hook-up) PMTs, for a total of 64 PMTs. Using the 3×3 position-encoding fiber optic bundle allows a base-4 hook-up for each of the x- and y-position banks (4 rows of 4 PMTs each allows encoding of $4^4=256$ positions), for a total of only 32 PMTs. Experimentation would be needed to see whether image and quantitation improvement from the theoretical improvement in PMT statistical response is large enough to warrant the increase in number of PMTs.

For the above 2×2 position-encoding fiber set hook-up, a total of 4096 or 64×64 fibers are attached to each PMT. For 1 mm by 1 mm SFOs these position-encoding fibers would be (slightly less than) 0.5 mm by 0.5 mm each at the attachment site to each SFO. Even without tapering, a fiber bundle of approximately 3.2 cm by 3.2 cm (or smaller diameter if arranged circularly) would be attached to each PMT, entirely feasible with most PMTs in existence. For the above 3×3 position-encoding fiber set hook-up a total of 16,384 or 128×128 fibers are attached to each PMT. These fibers would be approximately 0.33 cm by 0.33 cm each at each SFO attachment. Without tapering, a fiber bundle of approximately 4.2 cm by 4.2 cm (or smaller diameter if arranged circularly) would be attached to each PMT, also entirely feasible with most PMTs in existence. No need for tapering would allow easy matching of lengths of all position-encoding fibers, assisting coincidence circuitry. Even if tapering is needed, lengths of these fibers should be matched to assist in this. PMTs should ideally have uniform response across their faces. If not, then the 2×2 position-encoding fiber bundle hook-up would offer an advantage over the 3×3 hook-up, if no tapering were used. With appropriate tapering, this advantage disappears.

Despite the above theoretical advantages mentioned for 2×2 position-encoding fiber optic bundles, 3×3 bundles may still prove to be empirically adequate for symmetry, statistics and ease of hook-up. Certainly, fewer PMTs would be needed. It is not likely that this will hold for 4×4 or higher bundle numbers. However, this needs to be evaluated experimentally.

A significantly greater savings in position-encoding PMTs for base 2 can be achieved by not using any PMT to designate a zero in any bank. The coincidence circuitry would merely assign a zero to a position bank if no signal were received by the remaining PMT in that bank. The above base 2 hook-up would then have the x-positions encoded by one PMT in each of the units ($2^0$), 2s ($2^1$), . . . , and 128s ($2^7$) position banks, for a total of 8 PMTs. Including the y-positions, a total of only 16 PMTs would be needed. However, the fibers not used for position encoding would then have to be attached to another PMT (or set of PMTs) used for helping determine energy. If these fibers were not so hooked up, then a random loss of scintillation photons would result, making it difficult or impossible to calibrate for photon energy. For bases higher than 2, such omission of zero-encoding PMTs in each bank would also result in savings of position-encoding PMTs, but not as great a relative savings as in base 2. The fibers not used for position encoding would again have to be attached to energy-assessing PMTs. Depending on the number of positions in total and the number of fibers attachable to a PMT, this added complication in hook-up may not be warranted. Such an encoding would also not allow adequate rejection of unacceptable signals (see below).

The x- and y-positions need not be determined by separate banks of PMTs for each. If the total number of positions to be encoded is $N^2$ and the number of fibers in each position-encoding fiber optic bundle is f, then the number P of PMTs per bank row (the base used) that suffices is the smallest integer that satisfies $P^f \geq N^2$. An extra step would be needed in electronically decoding positions for this technique. If $N=2^f$, then the same total number of PMTs suffices for this hook-up as well as the separate banks technique.

No matter which above position-encoding system is used, the signal processor 32 would have to reject PMT signals that make no sense. For the above encoding using zero-position PMTs, one of the rejection criteria would occur during any time interval in which not exactly one PMT from each bank is producing a signal. Omitting the zero-position PMTs would not allow this.

Two or more scintillating fiber optic plates with their associated position-encoding fiber optic bundles and PMTs could be placed adjacent to each other to build up a larger field of view. However, it would be more efficient and less expensive to build a single fiber optic camera with the larger field of view.

For high enough flux of gamma rays (or radiation particles), the final resolution of the fiber optic gamma camera system would depend on a compromise between the technical capabilities of construction, camera response characteristics and acceptable imaging time. The great depth of interaction along the fibers would increase photon detection sensitivity (to near 100%), with more dramatic improvement noted for higher energy photons, and possibly more than make up for increased imaging time due to improved resolution, especially for high energy photons or other radiation. This would be a great boon to PET imaging without dedicated past art PET camera systems.

With dynamic collimators, resolution is determined solely by hole size. Since sensitivity for (both past art collimators and) dynamic collimators is determined, for the most part, by the ratio of hole size to septum thickness, for given hole length, sensitivity of dynamic collimators can be increased by reducing septum thickness, without affecting resolution, provided septal thickness remains great enough to stop the photons (or other particles). A dynamic collimator for low energy photons can have thinner septa and therefore higher sensitivity than one for high energy photons, and yet have the same resolution. This allows production of same resolution dynamic collimators for different energy photons, all having maximum sensitivity for the energy (photons) under consideration. If cost is not a problem, but patient throughput is, then having such a set of dynamic collimators for desired resolution would be helpful.

Prior art Anger gamma cameras are very limited in quantitating amount of radiation when imaging high photon flux sources. Part of this is due to non-linear response caused by dead time, time during which response relative to flux is reduced, and shows diminishing detected flux for high flux. The total dead time has components due to response by crystal, PMTs and the rest of the electronics/computer. The major component of PMT dead time in Anger gamma cameras is due to the fact that each PMT sees photons from the entire crystal. Cutting down the number of scintillation photons seen by each PMT would be of help. The fiber optic camera lends itself well to this, in that only a small part of the imaging field of view needs be connected by fibers to any PMT.

The holes in a dynamic collimator should be aligned at the same angle as the fibers in a fiber optic gamma camera in order to avoid penetration of photons across fibers and resultant degradation of resolution. This allows slant-hole dynamic collimators to be used with slant-fiber cameras (either planar or cylindrical) and converging/diverging dynamic collimators to be used with converging/diverging-fiber cameras. However, there would appear to be little use for such specialized set-ups at the present time, especially since the equipment would not lend itself well to general imaging.

The fiber optic camera of the subject invention has major advantages over past art Anger gamma cameras. These include, but are not limited to, much improved resolution, much improved sensitivity to higher energy photons (or whatever ionizing radiation is being detected), much improved linearity of response, much reduced dead time and improved energy resolution. Some of these are also advantages over past art fiber optic radiation detectors and ZnCdTe cameras.

The use of dynamic collimators described in the applicant's co-pending application would maximize the improvement in resolution. Improved resolution would increase lesion-to-background detected differences in radioactivity by reducing the volume-averaging effect and thereby would increase sensitivity for detecting abnormalities and would also be expected to increase specificity of diagnosis.

The described fiber optic camera, together with a dynamic collimator, can be used for detection or imaging of any ionizing photons or particles, in emission or transmission modes and in a wide energy band. This can be done in medical imaging or industrial non-destructive testing such as testing of uniformity of metal casting, looking for fatigue cracks in equipment components or distribution of radioactive components in nuclear fuel rods.

A large scintillating crystal, as in past art Anger gamma cameras, is not needed, so fine temperature control to prevent a cracked crystal is no longer needed. Temperature control (reduction) may still be necessary to reduce PMT voltage fluctuation and dark current. Dark current in a PMT is due to thermal emission of electrons from the scintillating coating on the inside of the PMT window. Its elimination or reduction is only needed with very low flux gamma rays or when very high resolution or highly accurate statistics in radiation counts is desired.

It should be understood that various modifications can be made to the preferred embodiments described and illustrated herein, without departing from the subject invention, the scope of which is defined in the appended claims.

I claim:

1. Apparatus for capturing a two dimensional image created by particle emanations from a source, comprising:
   a) collimator means for collimating the particle emanations and producing collimated emanations, comprising a collimator plate having a series of collimator apertures separated by septa made of a material capable of absorbing the emanations;
   b) scintillating means aligned behind the collimator means for capturing the collimated emanations and emitting scintillation photons corresponding thereto, comprising a two-dimensional array of scintillating fibers, wherein each scintillating fiber is located at a pre-selected x-position and y-position having x and y coordinates in an x-y plane; and
   c) position encoding means for encoding the x-y position of an active scintillating fiber receiving a particle emanation within a pre-selected time interval, comprising photon detecting means for detecting the emitted scintillation photons and generating output signals correlatable therewith, optical coupling means for optically coupling each scintillating fiber to the photon detecting means in a manner which encodes the x-y coordinates of the scintillating fibers, and signal processing means for processing the output signals and generating position signals indicative of the encoded position of the active scintillating fiber.

2. The apparatus defined in claim 1, wherein the optical coupling means comprises a network of optical fibers.

3. The apparatus defined in claim 2, wherein the network of optical fibers comprises sets of position fibers optically coupled to each individual scintillating fiber representing the x and y coordinates of the position thereof.

4. The apparatus defined in claim 3, wherein the photon detecting means comprises banks of photon detectors, wherein each bank of photon detectors comprises a plurality of individual photon detectors.

5. The apparatus defined in claim 4, wherein the sets of position fibers comprise individual position fibers having input ends coupled to the scintillating fiber and output ends coupled to a pre-selected combination of individual photon detectors representing the coordinates of the position of the scintillating fiber.

6. The apparatus defined in claim 5, wherein each scintillating fiber has a front imaging face positioned to receive the collimated emanations and a rear emitting face for emitting the scintillation photons, and the input ends of the individual position fibers are coupled to the rear emitting face of the scintillating fibers.

7. The apparatus defined in claim 4, wherein the individual photon detectors comprise photomultiplier tubes.

8. The apparatus defined in claim 4, wherein the banks of photon detectors comprise an x-bank of photon detectors and a y-bank of photon detectors, and the sets of position fibers comprise sets of x-position fibers coupled to the x-bank of photon detectors and sets of y-position fibers coupled to the y-bank of photon detectors.

9. The apparatus defined in claim 8, wherein the position coordinates of each scintillating fiber are assigned a value expressed in a base having a pre-selected number of places, wherein each of the places has a range of values, and the individual position fibers represent the place and value of the position coordinates of the scintillating fiber.

10. The apparatus defined in claim 9, wherein the individual photon detectors are identified as if arranged in an array of rows and columns, and the individual detectors in each row of the array represent one of the pre-selected places of the position coordinates and the individual detectors in the columns of each row represent one of the value in the range of values for the coordinates.

11. The apparatus defined in claim 1, wherein the signal processing means comprises coincidence detection means for detecting when exactly one scintillating fiber emits scintillation photons within the pre-selected time interval.

12. The apparatus defined in claim 11, wherein the processing means comprises an electronic or computer processor comprising means for analyzing the output of the rows of individual photon detectors to determine the position of the active scintillating fiber.

13. The apparatus defined in claim 9, wherein the base is base 10.

14. The apparatus as defined in claim 13, wherein each bank of photon detectors comprises at least three rows of individual photon detectors, wherein each of the rows comprises ten individual detectors, and wherein the detectors in the first of the rows represents values from 0 to 9, the detectors in the second of the rows represents values from 00 to 90, and the detectors in the third of the rows represents values from 000 to 900.

15. The apparatus as defined in claim 14 comprising a fourth row of individual photon detectors, representing values from 0.0 to 0.9.

16. The apparatus defined in claim 10, wherein the base is base 2.

17. The apparatus defined in claim 1, wherein the scintillating fibers comprise an outer layer of conducting material and a thin conducting central electrode, the outer layer being capable of being negatively charged relative to the central electrode.

18. The apparatus defined in claim 1, wherein the scintillating fibers comprise a thin conducting central electrode capable of being positively charged relative to ground.

19. The apparatus defined in claim 1, wherein the particle emanations are gamma rays.

20. The apparatus defined in claim 1, wherein the scintillating fibers comprise an outer coating that gives off photons detectable by the photon detection means when excited by electrons.

21. The apparatus defined in claim 1, wherein the optical fibers not needed for position encoding are connected to the photon detection means for purposes of more complete detection of scintillation photons.

22. The apparatus defined in claim 1, wherein the scintillation means comprises a plate configured for holding the array of scintillating fibers.

23. The apparatus defined in claim 22, wherein the plate and position encoding means are manufactured in smaller units for later assembly into a larger assembly.

24. The apparatus defined in claim 4, wherein the individual photon detectors comprise large area array photodiodes.

* * * * *